United States Patent [19]

Welker

[11] Patent Number: 5,531,130
[45] Date of Patent: Jul. 2, 1996

[54] PIPELINE SAMPLING ENCLOSURE

[76] Inventor: Brian H. Welker, 13818 Florence, Sugar Land, Tex. 77478

[21] Appl. No.: 429,350

[22] Filed: Apr. 26, 1995

[51] Int. Cl.⁶ ................................................ G01N 1/00
[52] U.S. Cl. ................................ 73/863.81; 73/863.11
[58] Field of Search ......................... 73/863.11, 863.12, 73/863.81–863.86, 864.34, 431, 866.5, 201, 756; 248/231

[56] References Cited

U.S. PATENT DOCUMENTS

| | | | |
|---|---|---|---|
| 2,404,087 | 7/1946 | Parsons | 73/298 |
| 3,212,339 | 10/1965 | Olmedo | 73/431 |
| 3,443,436 | 5/1969 | Meyer | 73/273 |
| 3,731,534 | 5/1973 | Painley et al. | 73/273 |
| 3,793,887 | 2/1974 | Anderson et al. | 73/863.11 |
| 4,010,648 | 3/1977 | Harris, Jr. et al. | 73/863.85 |
| 4,193,420 | 3/1980 | Hewson | 73/201 |
| 4,232,736 | 11/1980 | Pillette | 166/53 |
| 4,403,517 | 9/1983 | Thomte | 73/863.84 |
| 4,475,410 | 10/1984 | Jaeger | 73/863.84 |
| 4,934,200 | 6/1990 | Lantz | 73/863.85 |
| 4,957,251 | 9/1990 | Hubbard | 248/231 |
| 4,974,453 | 12/1990 | Hohorst | 73/863.11 |

*Primary Examiner*—Robert Raevis
*Attorney, Agent, or Firm*—Herzog, Crebs & McGhee

[57] ABSTRACT

A housing for a pipeline sampling apparatus is mounted upon the pipeline wherein a sample is to be taken. The housing encloses the sampling pump and probe, and the sample cylinder, while allowing easy access to the interior in order to exchange the sample cylinder. Preferably, the housing surrounds at least 40% of the pipe section where the housing is installed. By mounting the sample cylinder within the housing next to the pipeline, the sample cylinder is kept at nearly the same temperature as the fluid flow within the pipeline. Also, all of the sampling components are protected from the elements. Additionally, the sample cylinder may be supported by the housing.

8 Claims, 7 Drawing Sheets

PIPELINE SAMPLING ENCLOSURE

FIELD OF THE INVENTION

The present invention relates generally to apparatuses for the sampling of pipeline contents and, more specifically, to a housing for the sampling components.

BACKGROUND OF THE INVENTION

It is well established that certain commodities, such as oil and natural gas, are priced according to their BTU (British Thermal Units) content per volume. The more BTU's the oil or gas can produce, the higher its price. Accordingly, the lower the BTU content, the lower its price. Also, it is useful to monitor the output of the source in order to determine the overall worth of the oil or gas well.

In order to determine the BTU content per a given volume of the gas or liquid, it is necessary to analyze the gas or liquid. Ideally, the gas or liquid would be continuously analyzed. This is because the BTU content may and generally does change with time. However, because it is not possible to continuously analyze the gas or liquid, periodic samples are taken and stored within a sample collection cylinder. Once the sample collection cylinder is full, it is taken to a laboratory where the gas or liquid is analyzed for its BTU content. In this manner, an average BTU content is determined for a given period of time upon which pricing of the gas or liquid may be based.

The sample is taken from the oil or gas pipeline by a sampler or sample pump that is either mounted directly onto the pipeline or is remote therefrom. In the case of direct mount, a probe generally extends into the pipeline for sample collection with the sampler timed to periodically receive and store the sample within the sample cylinder. In the case of a remote mount, a line or conduit extends into the pipeline and communicates with the sampler to provide the necessary sample.

In the prior art the sample collection cylinder was remote from the pipeline and sampler and exposed to the elements. This arrangement facilitated the exchange of sample collection cylinders when the old sample collection cylinder was full. However, it has been found that for optimum sample storage within the sample collection cylinder, the sample collection cylinder should be maintained at or near the same temperature as the liquid or gas flowing within the pipeline.

By maintaining the sample collection cylinder at or near the same temperature as the flowing gas or liquid, the volume of the sample received in the sample collection cylinder will be the same volume as sampled. Further the total sample volume of the sample collection cylinder will remain nearly constant.

In the prior art it is known to enclose the sampler or sample pump within a housing in order to alleviate the possibility of contaminants entering and mixing with the sample, as well as protect the sampler or sample pump itself from the elements. The other components of the sampling apparatus are remote from the pipeline and exposed to the elements.

It would thus be advantageous to have the sample collection cylinder and its eventual contents to be maintained at essentially the same temperature as the gas or liquid flowing within the pipeline.

SUMMARY OF THE INVENTION

The present invention alleviates the problems encountered with exposed sampling equipment and especially the sample collection cylinder by providing an enclosure or housing for all of the sampling components. The enclosure at least partially surrounds the pipe section where the sampler is located. The sample collection cylinder is thus housed adjacent to the pipe section and is protected from the elements. In this manner, the sample collection cylinder is maintained at approximately the same temperature as the gas or liquid flowing within the pipeline.

In one form thereof, the sampling enclosure includes a top and bottom portion that are connected in a manner to allow access to the interior thereof. The bottom element is sized to at least partially surround the pipe section. The housing is sized to accommodate all of the sampling components, including the sample collection cylinder.

At least 40%, and preferably more, of the pipe section is covered or surrounded by the sampling enclosure. This allows the temperature of the interior atmosphere of the enclosure to approximately equal the temperature of the pipeline, or its contents which in turn is conducted to the sample collection cylinder.

The enclosure is fastened to the pipeline by various methods, depending on the style of the enclosure and the diameter of the pipeline. Generally, the enclosure includes integral flanges or portions that help support the enclosure on the pipeline or that provide an attachment means.

BRIEF DESCRIPTION OF THE DRAWINGS

So that the manner in which the above-recited features, advantages, and objects of the present invention are attained and can be understood in detail, a more particular description of the invention, briefly summarized above, may be had by reference to the embodiments thereof which are illustrated in the appended drawings.

It is noted, however, that the appended drawings illustrate only typical embodiments of this invention and are therefore not to be considered limiting of the scope of the invention, for the invention may admit to other equally effective embodiments. Reference the appended drawings, wherein.

DETAILED DESCRIPTION

Figure 1:
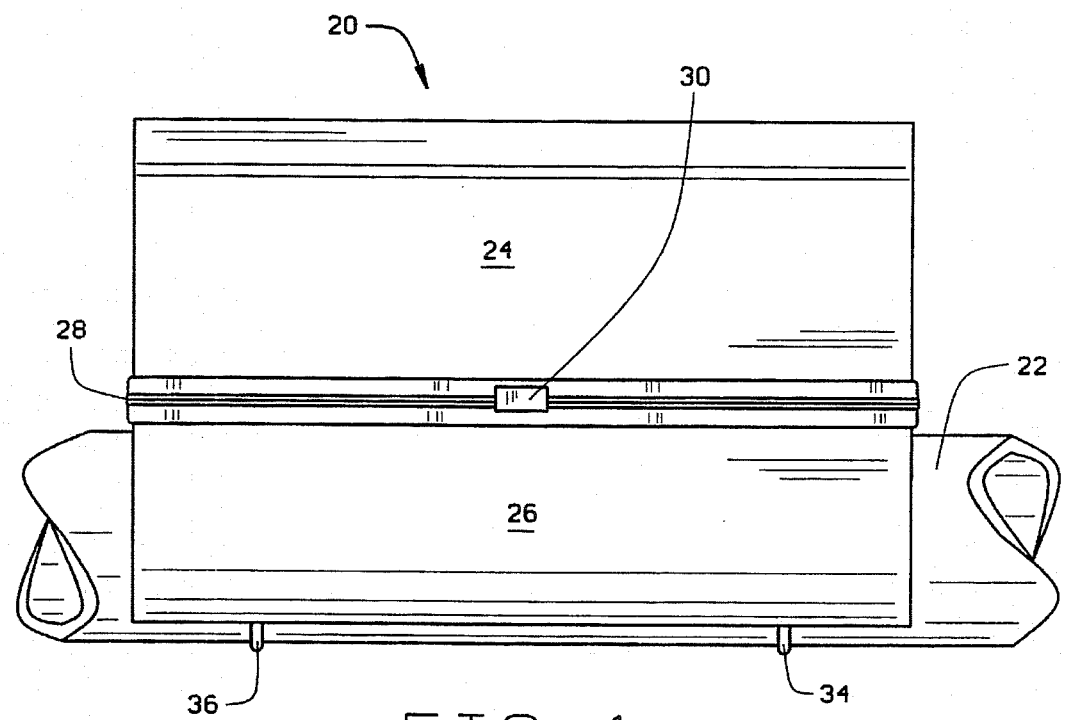
FIG. 1 is a front elevation view of the present sampling enclosure mounted on a section of pipe.
Figure 2:
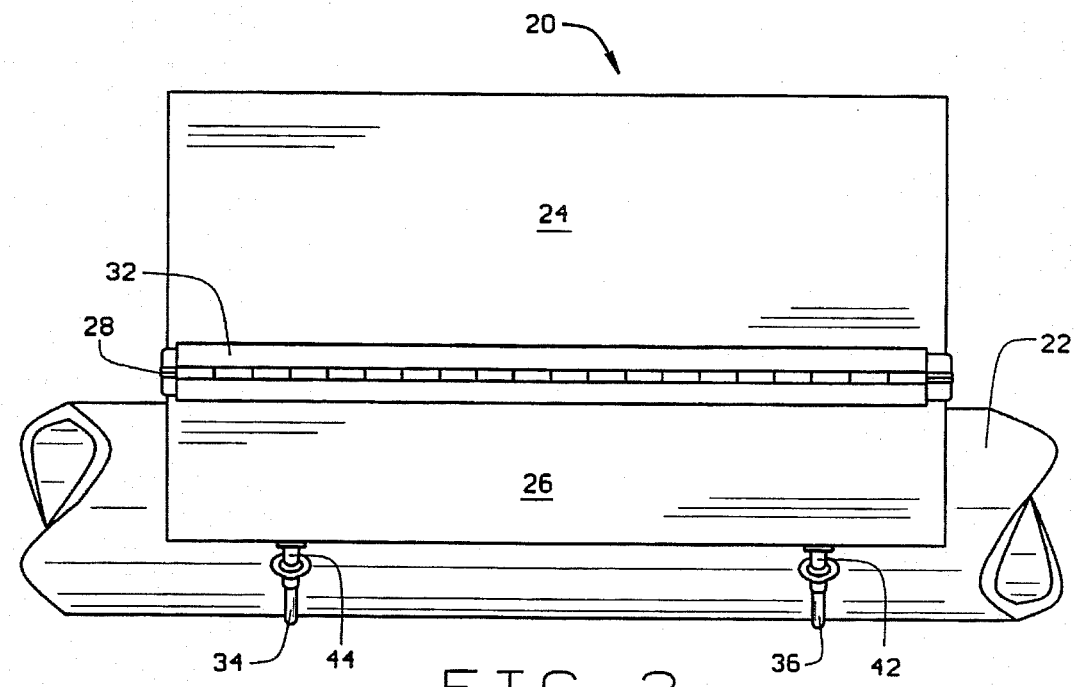
FIG. 2 is a rear elevation view of the present sampling enclosure mounted on the section of pipe.
Figure 3:
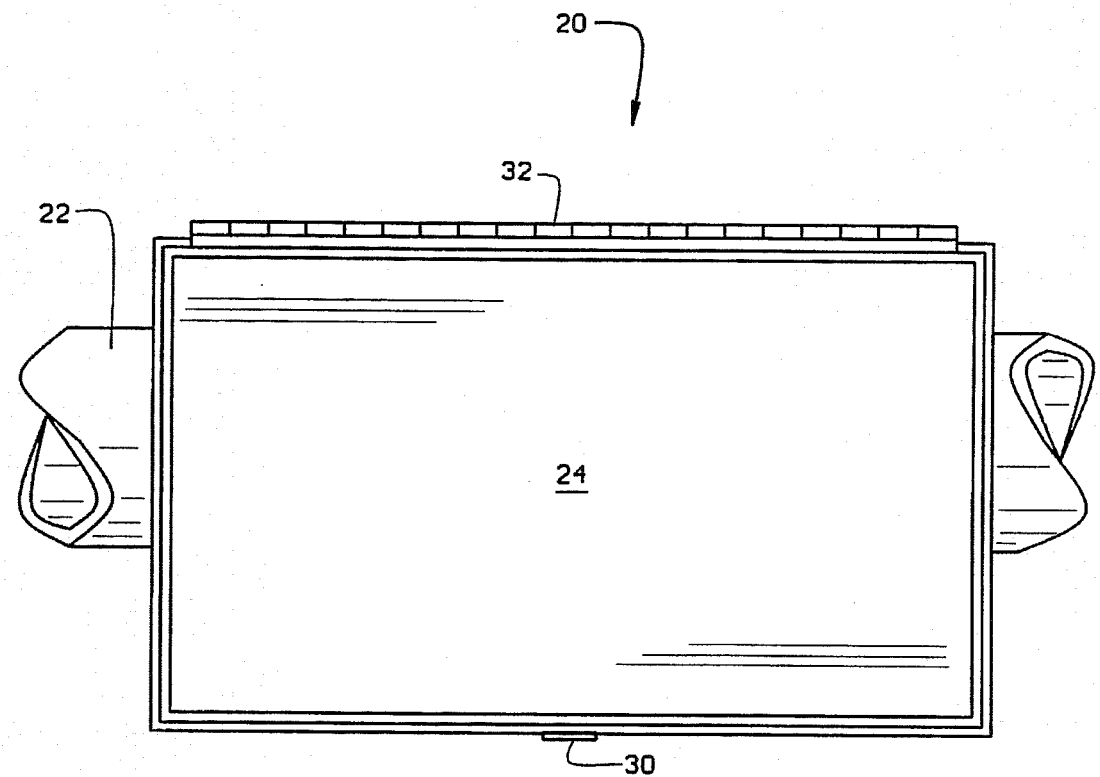
FIG. 3 is a top plan view of the present sampling enclosure mounted on the section of pipe.
Figure 4:
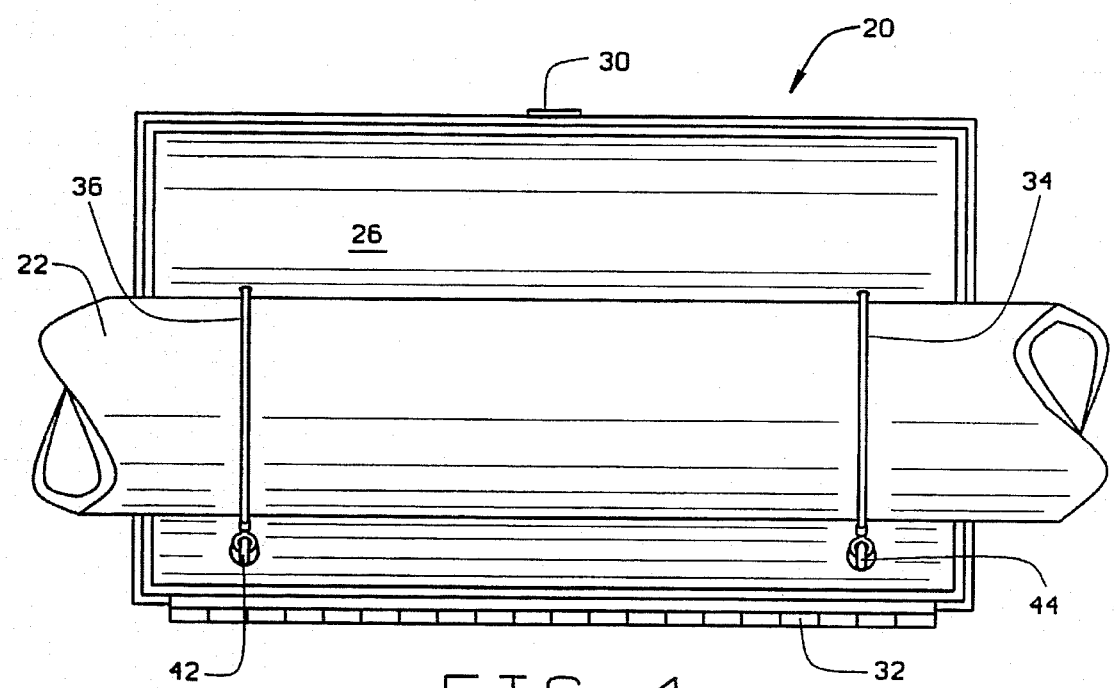
FIG. 4 is a bottom plan view of the present sampling enclosure mounted on the section of pipe.

Referring now to FIGS. 1–5, there is depicted an embodiment of a pipeline sampling apparatus enclosure generally designated 20 shown mounted on a section of pipe 22. The pipe section 22 is representative of a portion of a pipeline generally carrying a gas or liquid, e.g. natural gas or oil, wherein such contents of the pipeline needs to be periodically sampled. The enclosure 20 has a top or upper half 24 and a bottom or lower half 26 that are situated to meet at a juncture 28. Preferably, the enclosure is made of fiberglass or similar material that would resist the elements and provide a weather resistant housing.

Connected to the top half 24 and the bottom half 26 between the juncture 28 is a hinge 32 that allows the top half 24 to pivot with respect to the bottom half 26. The hinge 32 is shown as extending the length of the rear of the halves 24, 26 for stability when opening the enclosure 20, although a plurality of hinges or other similar mechanisms may certainly be utilized to allow the halves to be opened. Alternatively, the halves 24, 26 may be connected so that one half may be removed from the other half. Disposed opposite to the hinge 32 on the front of the enclosure 20 is a latch or clasp 30 that extends across the juncture 28. The latch 30 is adapted to releasably close together the top half 24 to the bottom half 26.

The bottom half 26 is stabilized by and partially held onto the pipe section 22 by two straps 34 and 36 that extend between a front rounded portion 38 and a rear rounded portion 40 of the bottom half 26 underneath the pipe section 22. With additional reference to FIG. 6, the front rounded portion 38 is formed by a rounded bottom wall 46 that includes an upwardly extending segment 47 that is contoured to form around at least a portion of the pipe section 22. The rear rounded portion 40 likewise includes an upwardly extending segment 49 that is contoured to form around at least a portion of the pipe section 22. The upward extending portions 47 and 49 coact to allow the bottom portion 26 to rest upon the pipe section 22.

One end of each of the straps 34, 36 is coupled to the upwardly extending segment 47, while the other end is coupled via hooks 44 and 42, respectively, to the upwardly extending segment 49. In this manner the bottom half 26 straddles the upper portion of the pipe section 22 and is clamped thereto by the straps 34, 36. The bottom portion 26 thus rests upon the pipe section 22 through contact with the wall portions 47 and 49. Obviously, the wall portions 47 and 49 may be sized to accommodate various diameters of a pipe section 22.

The enclosure is designed to house the sampling components, and especially the sample cylinder, from the outside elements or weather and maintain those components at approximately the same temperature as the flowing liquid or gas within the pipeline. Preferably, the enclosure surrounds at least 40% of the pipeline while still housing the sampler and sample cylinder.

Figure 6:
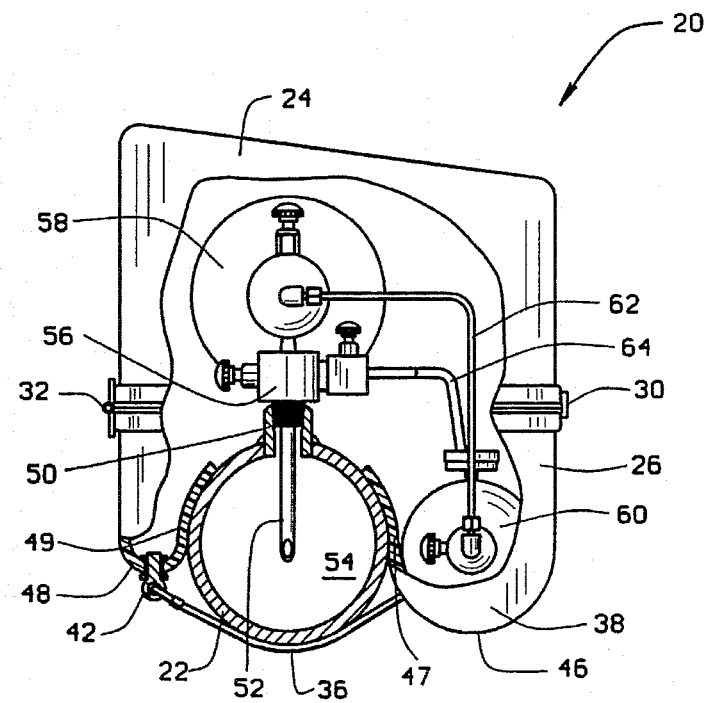
FIG. 6 is a partial cutaway right side view of the present sampling enclosure showing the internal coupling of the sampling enclosure to the pipe and the position of the various sampling components therein.
Figure 7:
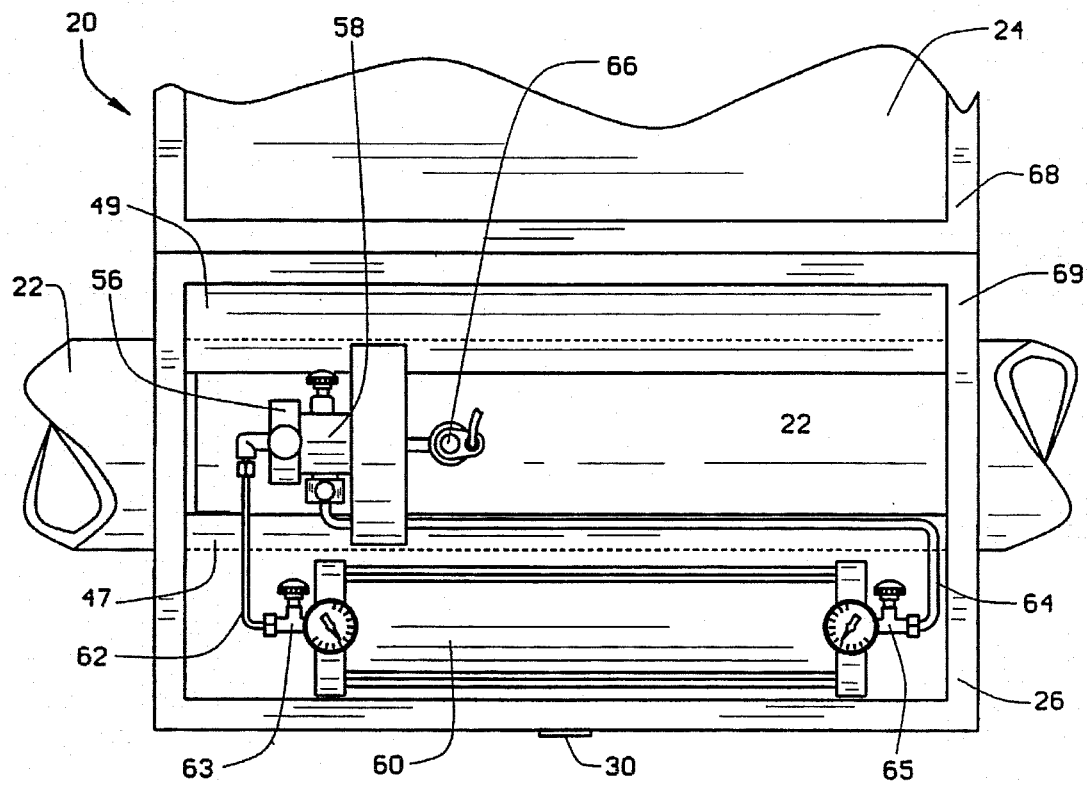
FIG. 7 is a top plan view of the present sampling enclosure mounted on the pipe in an open position showing the location of the various sampling components.
Figure 5:
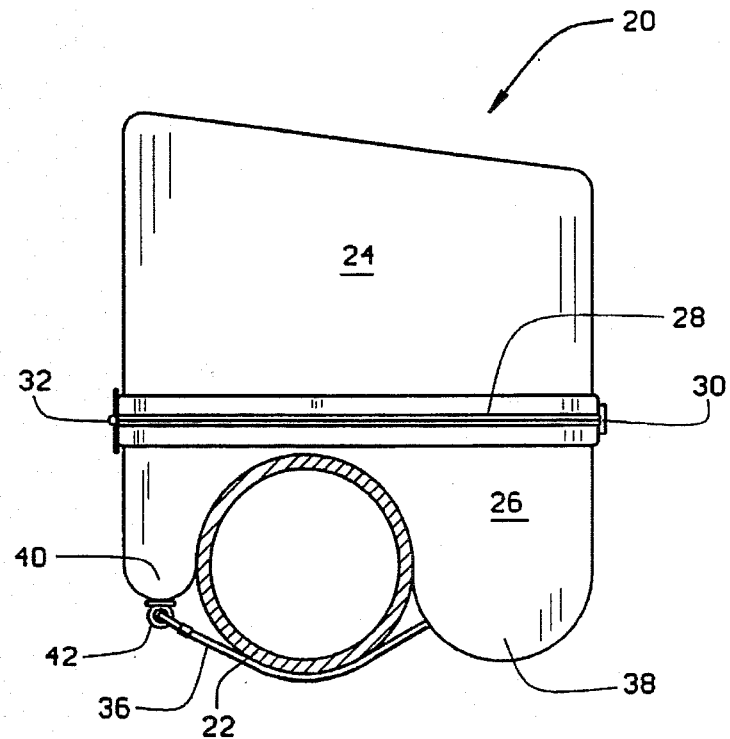
FIG. 5 is a right side view of the present sampling enclosure mounted on the section of pipe.

FIGS. 6 and 7 depict the positions of the various sampling components within the enclosure 20. The pipe section 22 includes a threaded opening 50 such as a Weld-O-Let™ or the like in which is threadedly received a probe mount 56 of a probe-type sampler 58. The sampler 58 includes a probe 52 that extends from the probe mount 56 into the interior 54 of the pipe section 22 through the opening 50. Disposed within a pocket defined by the front rounded portion 38 is a sample collection cylinder 60. While the sample collection cylinder 60 may be of any type, it is shown as a constant pressure collection cylinder. The probe 58 is in communication with the cylinder 60 through a sample outlet tube or conduit 62 via a valve/gauge 63 wherein the sample taken from the pipeline is caused to flow into the cylinder 60. The opposite end of the cylinder 60 is coupled to the sampler 58 via a precharge tube or conduit 64 and valve/gauge 65.

With particular reference to FIG. 7, the sampler 58 generally includes a solenoid 66 that is coupled to an electrical source so that an RTU or timer may be utilized with the sampler 58. Further, the upper and lower halves 24 and 26 each include a ledge 68, 69 respectively that define the juncture 28 when closed.

When it is desired to exchange a full cylinder 60 with an empty cylinder 60, fix or calibrate the sampler 58, it is merely a matter of unlatching the clasp 30 and raising the upper half 24 from the lower half 26 wherein the entire interior of the enclosure 20 is accessible.

Figure 8:
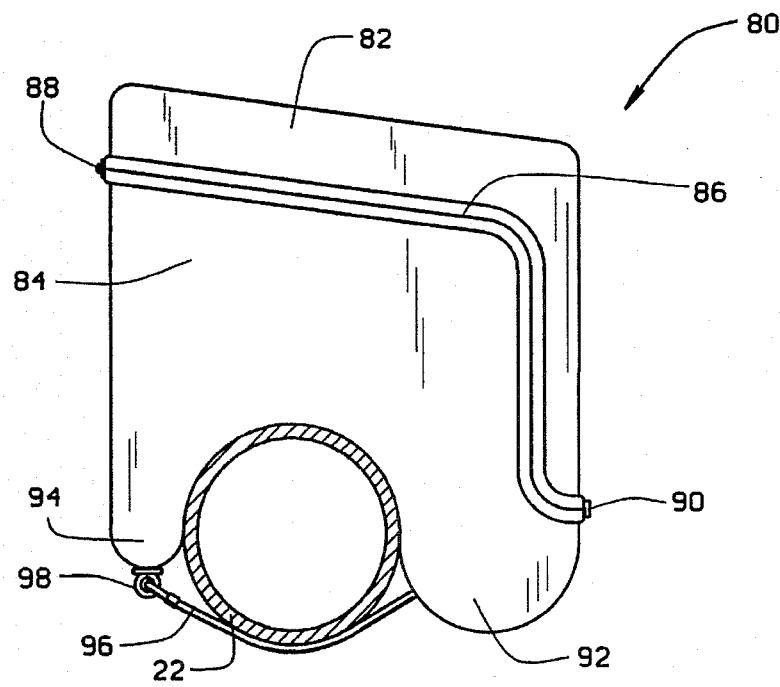
FIG. 8 is a right side view of the present sampling enclosure mounted on the section of pipe, showing an alternative juncture structure for the top and bottom halves.

With reference to FIG. 8, there is shown an alternative embodiment of the enclosure 20 of FIGS. 1–7 mounted upon the pipe section 22, generally designated 80. The enclosure 80 likewise includes an upper half 82 and a lower half 84. However, in this embodiment, the upper and lower halves 82, 84 meet along a curved juncture 86 thereby defining a tall lower half 84 and a short upper half 82. A hinge 88 is disposed on the rear of the halves 82, 84 between the juncture 86 while a clasp 90 is disposed at the front thereof. The lower half 84 includes a front rounded portion 92 and a rear rounded portion 94. Extending from the front rounded portion 92 underneath the pipe section 22 are two straps, of which only one strap 96 is shown, that terminate at the rear rounded portion 94 in hooks, of which only one hook 98 is shown.

It should be appreciated that this embodiment of the housing 80 holds the various sampling components in like manner to the housing 20 depicted in FIGS. 1–7.

Figure 9:
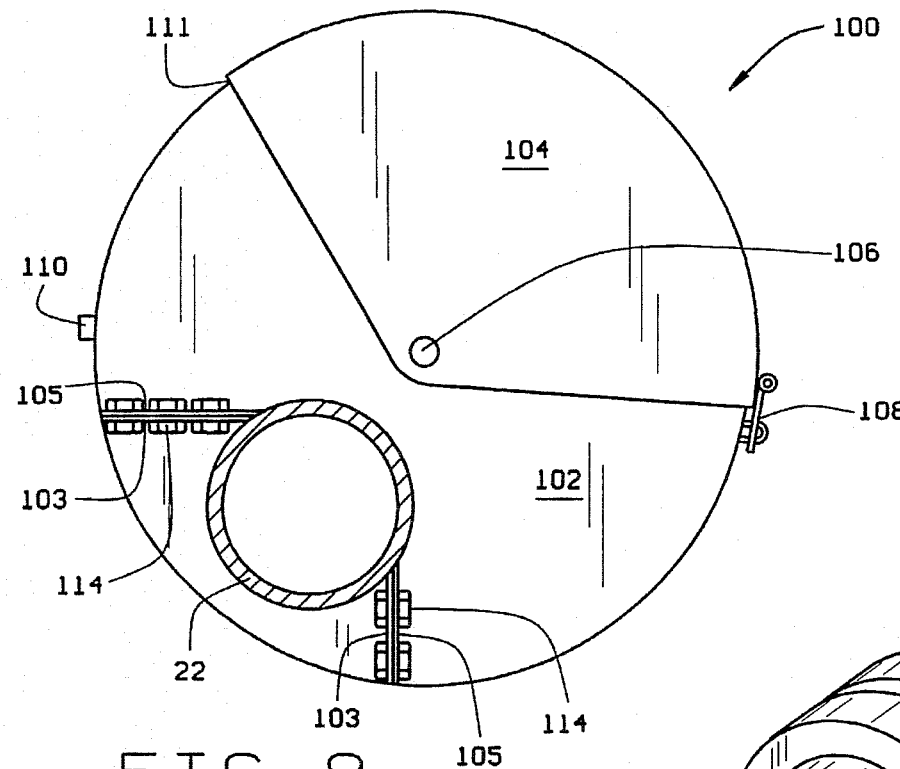
FIG. 9 is an alternative embodiment of a sampling enclosure that surrounds the pipe.

With reference now to FIG. 9 there is shown a further alternative embodiment of the housing or enclosure, here generally designated 100. The enclosure 100 is cylindrical in shape and includes a lower half 102 that completely surrounds the pipe section 22. A flange 103 is integral with the inside of the lower half 102. A band 105 extends around the pipe section 22 and couples to the flange 103 to hold the lower half 102 thereon. An upper half 104 is situated on the outside of the lower half 102 and includes a pivot 106 such that the upper half 104 may be moved relative thereto. A clasp or latch 108 is included on the upper and lower halves 104, 102 that allows the halves to be closed. The lower half 102 also includes a radially outwardly extending stop or protrusion 110 that is essentially radially opposite the clasp 108. The stop 110 is adapted to engage a portion 111 of the upper half 104 in order to prevent the upper half 104 from rotating too far about the lower half 102.

Figure 10:
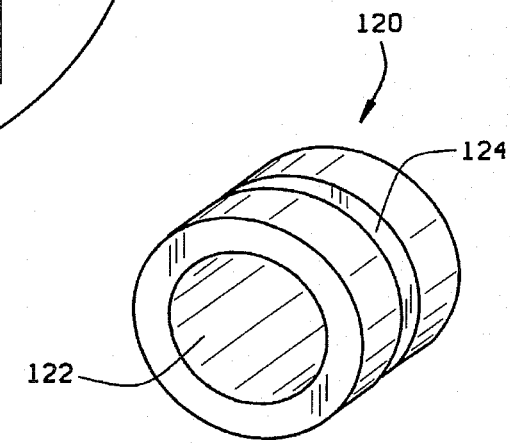
FIG. 10 is a perspective view of a core insert for the alternative sampling enclosure embodiment to be used for smaller diameter pipe.
Figure 11:
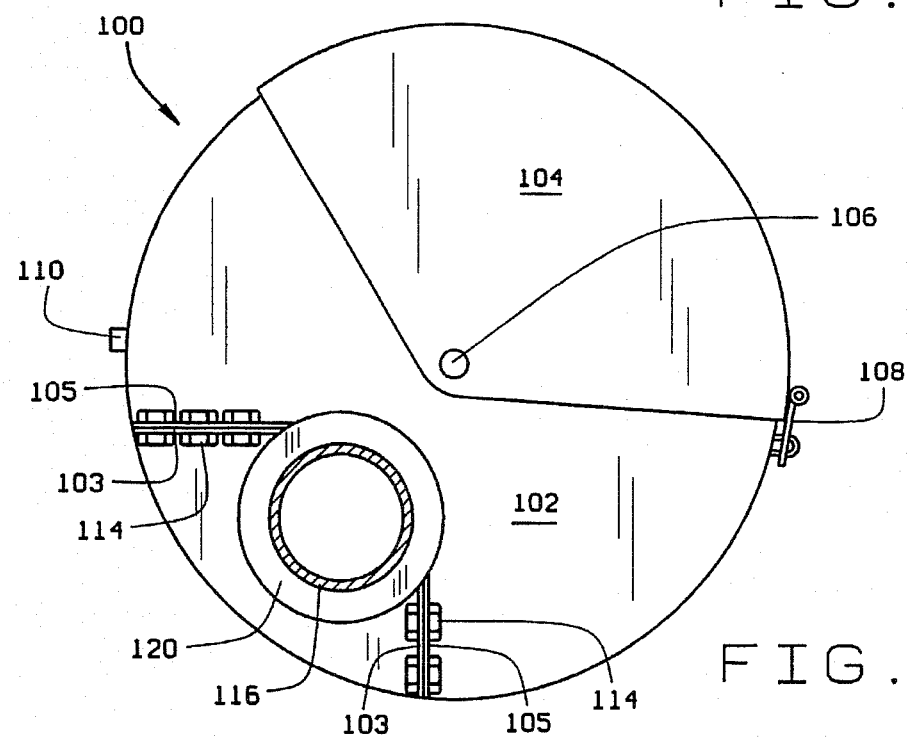
FIG. 11 is the alternative sampling enclosure embodiment of FIG. 9 with the core insert of FIG. 10, all mounted on the pipe.

Because not all pipelines are of the same diameter, it may be necessary to include a spacer or the like around the pipe section in order to adapt the specific mount to the pipe section. FIG. 10 depicts such a spacer, insert, or core generally designated 120. An adaption of the core may also be used to grip the pipe and allow the bands to be securely held onto the pipe. The core 120 is cylindrical and includes a cylindrical opening 122. Disposed on the outside of the core 120 is a band groove 124 that is adapted to hold the securing bands in place and prevent slipping. FIG. 11 shows the enclosure 100 about a smaller diameter pipe section 116 with the core 120 in place therearound. In this embodiment, the sample cylinder (not shown in FIGS. 9 and 11) is "free" within the enclosure 100.

Figure 12:
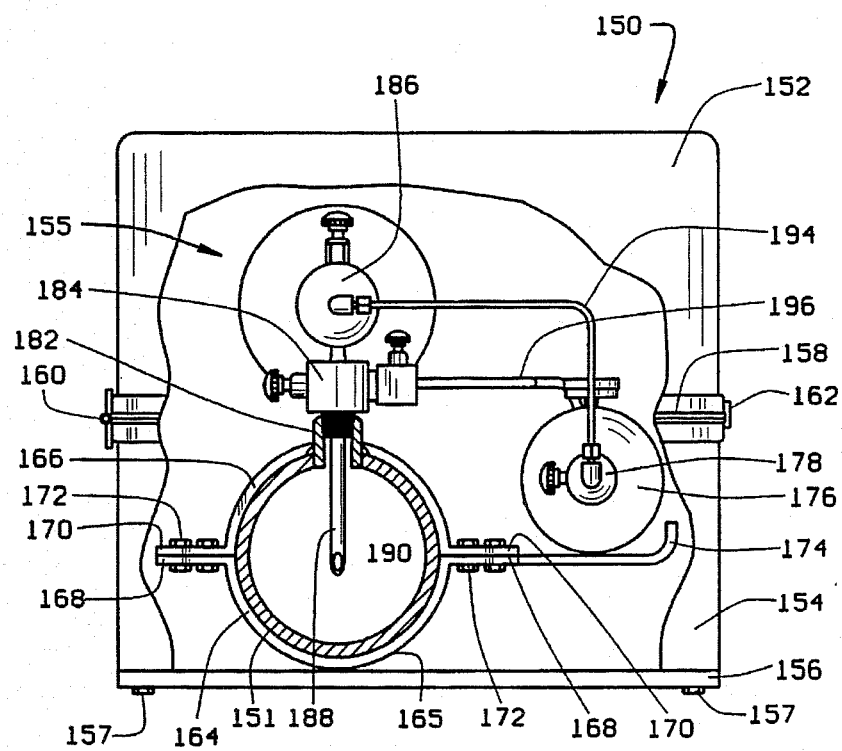
FIG. 12 is a cutaway side view of further alternative embodiment of the sampling enclosure mounted on a pipe.
Figure 13:
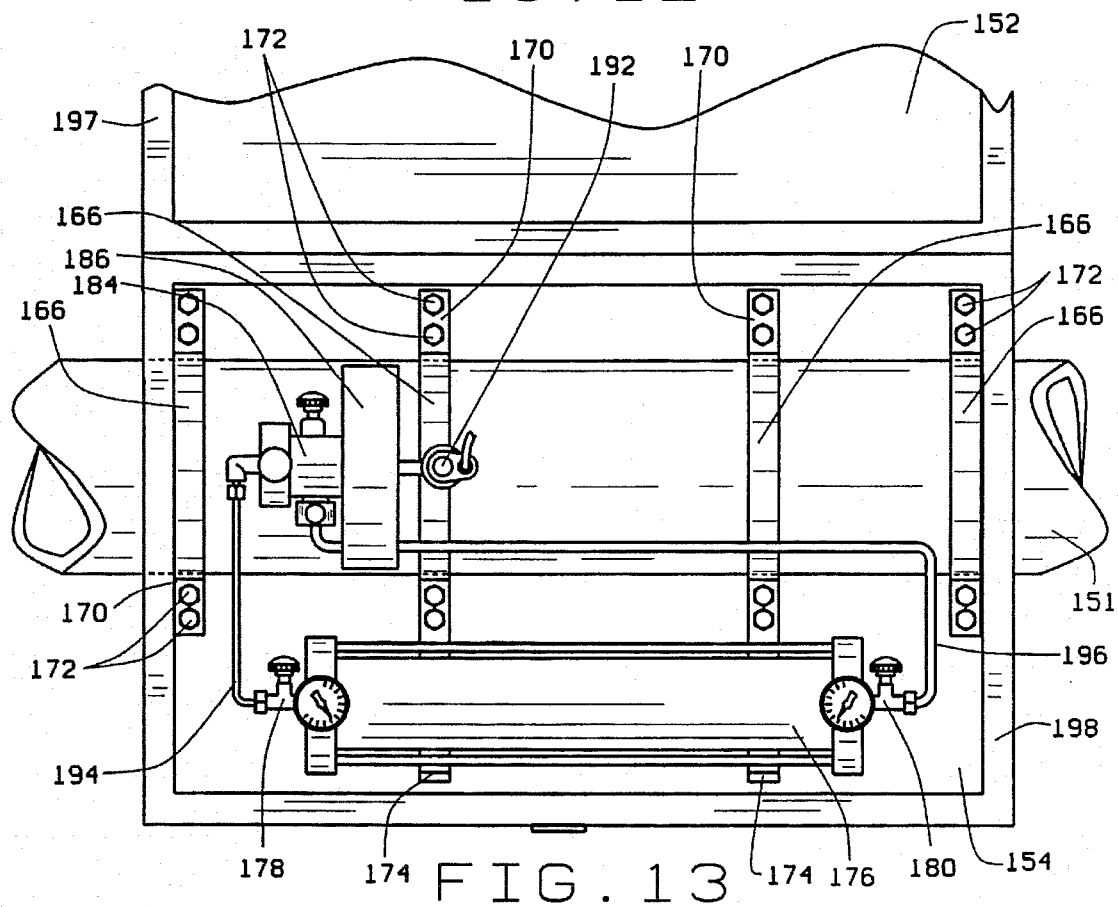
FIG. 13 is a top plan view the further alternative sampling enclosure embodiment of FIG. 12 with the top open.
Figure 14:
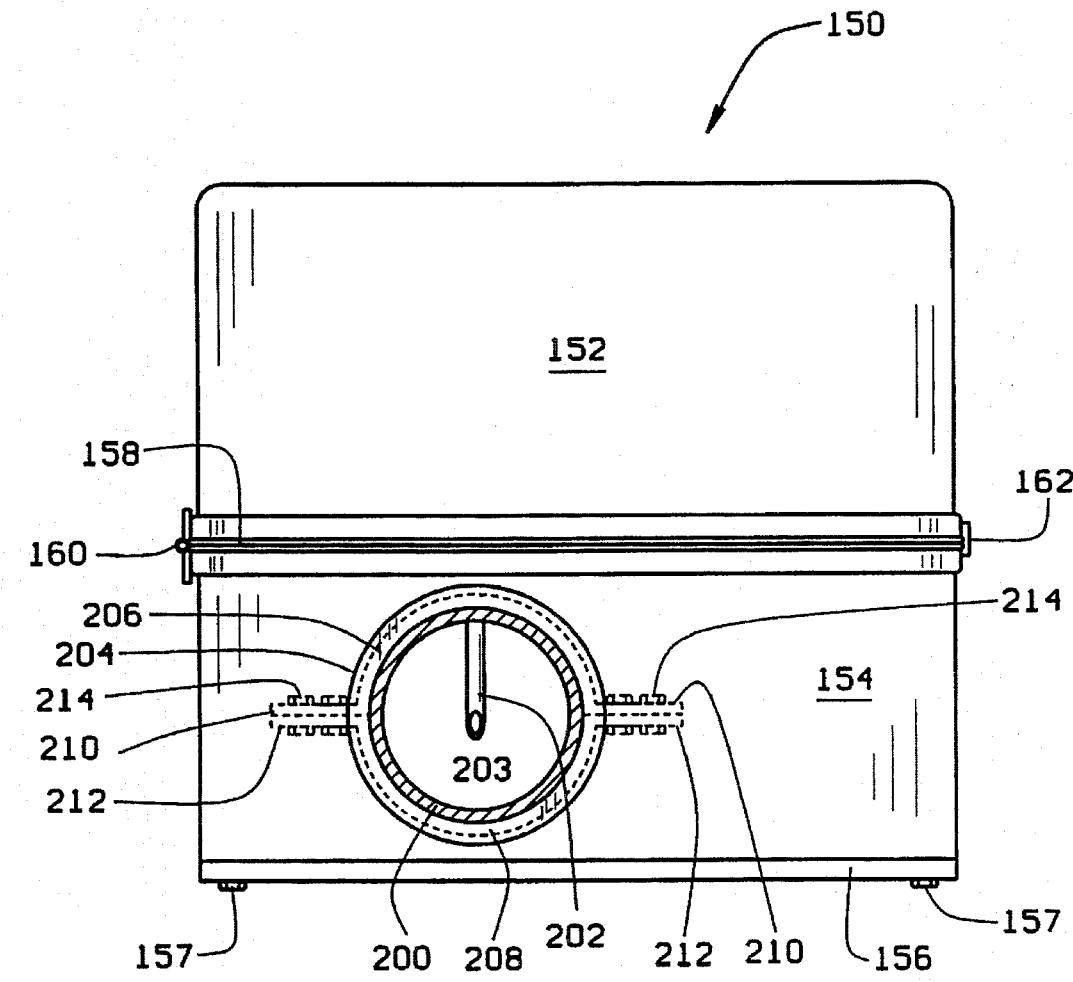
FIG. 14 is a side view of the further alternative sampling enclosure embodiment of FIG. 12 utilizing the core insert of FIG. 10.

An even further embodiment of the enclosure is depicted in FIGS. 12–14. A square enclosure 150 is shown surrounding a pipe section 151. The enclosure 150 includes an upper half 152 and a lower half 154 that meet at a juncture 158 and which surround the sampling components being generally designated 155. A hinge 160 is attached to the rear of the upper and lower halves 152, 154 to allow the upper half 152 to open relative to the lower half 154 as the lower half 154 is releasably fixed to the pipe section 151. Disposed opposite to the hinge 160 is a clasp or latch 162 to maintain the upper and lower halves 152, 154 together. Additionally, the clasp 162 may be of the type that allows a lock or is self-locking to prevent unauthorized tampering of the sampling components 155.

A bottom plate 156 is attached to the lower half 154 by a plurality of bolts or screws 157. A plurality of lower semicircular clamps or bands, of which only one such clamp 164 is shown, are attached to the bottom plate 156 by welding to a post or flat bar, or the like. The bands 164 encircle the bottom half of the pipe section 151. Complementary semicircular upper bands 166 are disposed on the top half of the pipe section 151. The lower bands 164 include flanges 168 on either side while the upper bands 166 include complementary flanges 170 on either side thereof. The lower and upper band flanges 168, 170 are held together by a bolts 172 or the like. In this manner, the bands clampingly retain or attach the bottom plate 156 and thus the lower half 154 of the enclosure 150 to the pipe section 151.

Additionally, extending from the bands 164, 166 are support brackets 174 that hold or on which rests a sample collection cylinder 176. The sample collection cylinder 176 is shown as a constant pressure cylinder and thus includes an inlet valve/gauge 178 and an outlet pressure valve/gauge 180. As per the typical sampling setup, the pipe section 151 includes an opening or Weld-O-Let™ 182 in which is threadedly received a probe mount/precharge valve 184. The probe mount/precharge valve 184 is coupled to a sampler or sample pump 186. A sample receiving probe 188 extends from the probe mount/precharge valve 184 into the interior 190 of the pipe section 151. The sampler may be operated by a solenoid 192 in like manner to the solenoid 66 of FIG. 7.

The sample is sent to the cylinder 176 via a sample outlet line 194 that is releasably coupled to the valve 178. A constant pressure line 196, releasably coupled to the valve 180, is coupled at the other end to the sampler 186.

Additionally, in FIG. 13, the upper half 152 includes a ledge 197 that abuts a corresponding ledge 198 of the bottom half 154.

With reference to FIG. 14 a smaller diameter pipe section 200 is shown in which a probe 202 extends into the interior 203 thereof. In like manner to the embodiment of FIGS. 10 and 11, a core or insert 204 surrounds the pipe section 200 with an upper clamp 206 and a lower clamp 208 encircling the insert 204. Upper clamp flanges 210 mate with lower clamp flanges 212 that are held together with bolts 214 to clampingly retain the enclosure 150 about the pipe section 200. A plurality of clamps are generally utilized along the pipe section 200. In like manner to the embodiment of FIGS. 12 and 13, the lower clamps 208 are welded to the bottom plate 156. FIG. 14 does not show the lower clamps 208 attached to the bottom plate 156 for clarity.

While the foregoing is directed to the preferred embodiment of the present invention, other and further embodiments of the invention may be devised without departing from the basic scope thereof, and the scope thereof is determined by the claims which follow.

What is claimed is:

1. A housing mounted on a pipeline to enclose a sampler and a sample cylinder, the pipeline containing a flowing fluid which has a temperature that is generally different from the ambient surrounding atmosphere, said housing comprising:

(a) a top element;

(b) a bottom element dimensioned to engage said top element, said top element and said bottom element together defining a housing which partially encircles the pipeline, said housing sized to enclose and isolate the sampler and the sample cylinder from the ambient surrounding atmosphere when mounted on said pipeline;

(c) opposed rims extending from and forming a part of said bottom element, said rims contacting said pipeline to support said housing, said rims exposing the interior atmosphere of said housing to a portion of the pipeline, so that the interior atmosphere and the sample cylinder are maintained at approximately the same temperature as the fluid flowing through said pipeline; and (d) a plurality of straps mounted on said bottom element to securely position and hold said bottom element on the pipeline.

2. The apparatus of claim 1 further including at least one connector, a portion thereof being mounted on said top element and a portion of said connector being mounted on said bottom element, said connector having an open position allowing said top element to be disengaged from said bottom element to gain access to the sampler and the sample cylinder and said connector also having a closed position allowing said top element to be securely attached to said bottom element.

3. A housing mounted on a pipeline to enclose a sampler and a sample cylinder, the pipeline containing a flowing fluid which has a temperature that is generally different from the ambient surrounding atmosphere, said housing comprising:

(a) a top element;

(b) a bottom element, said top element and said bottom element defining said housing;

(c) at least one hinge, a portion thereof connected to said top element and a portion connected to said bottom element, allowing said top element to move from a closed position to an open position to gain access to the sampler and the sample cylinder;

(d) said housing sized to enclose and isolate the sampler and the sample cylinder from the ambient surrounding atmosphere when mounted on said pipeline;

(e) opposed rims extending from and forming a part of said bottom element, said rims contacting said pipeline to support said housing and exposing the interior atmosphere of said housing to a portion of the pipeline, so that the interior atmosphere and the sample cylinder are maintained at approximately the same temperature as the fluid flowing through said pipeline; and (f) a plurality of straps mounted on said bottom element to securely position and hold said bottom element on the pipeline.

4. The apparatus of claim 3 further including a latch which can be locked when said top element is in the closed position and which can be unlocked when necessary to move said top element to the open position.

5. A housing mounted on a pipeline to enclose a sampler and a sample cylinder, the pipeline containing a flowing fluid which has a temperature that is generally different from the ambient surrounding atmosphere, said housing comprising:

(a) a top element;

(b) a bottom element dimensioned to engage said top element, said top element and said bottom element together defining a housing which completely encircles the pipeline, said housing sized to enclose and isolate the sampler and the sample cylinder from the ambient surrounding atmosphere when mounted on said pipeline, said top element and said bottom element completely encircling the pipeline;

(c) at least one clamp extending from and connected to said bottom element, said clamp gripping said pipeline to support said housing;

(d) support brackets that cradle the sample cylinder inside said housing; and (e) said top element and said bottom element exposing the interior atmosphere of said housing to at least a portion of the pipeline so that the interior atmosphere and the sample cylinder are maintained at approximately the same temperature as the fluid flowing through said pipeline.

6. The apparatus of claim 5 further including at least one connector, a portion thereof being mounted on said top element and a portion of said connector being mounted on said bottom element, said connector having an open position allowing said top element to be disengaged from said bottom element to gain access to the sampler and the sample cylinder and said connector also having a closed position allowing said top element to be securely attached to said bottom element.

7. A housing mounted on a pipeline to enclose a sampler and a sample cylinder, the pipeline containing a flowing fluid which has a temperature that is generally different from the ambient surrounding atmosphere, said housing comprising:

(a) a top element having an opening to accommodate pipelines with different diameters;

(b) a multi-part bottom element having an opening to accommodate pipelines with different diameters, said top element and said bottom element together defining said housing which completely encircles the pipeline;

(c) at least one clamp extending from and connected to said bottom element, said clamp gripping said pipeline to support said housing;

(d) support brackets that cradle the sample cylinder inside said housing; and (e) a plurality of inserts sized to surround a specific diameter pipeline, said inserts blocking said openings in said top element and said bottom element so that the interior atmosphere and the sample cylinder are maintained at approximately the same temperature as the fluid flowing through said pipeline.

8. The apparatus of claim 7 further including at least one connector, a portion thereof being mounted on said top element and a portion of said connector being mounted on said bottom element, said connector having an open position allowing said top element to be disengaged from said bottom element to gain access to the sampler and the sample cylinder and said connector also having a closed position allowing said top element to be securely attached to said bottom element.

* * * * *